United States Patent
Limbach et al.

(10) Patent No.: US 11,813,593 B2
(45) Date of Patent: Nov. 14, 2023

(54) HETEROGENEOUS CATALYST

(71) Applicants: Dow Global Technologies LLC, Midland, MI (US); Rohm and Haas Company, Collegeville, PA (US)

(72) Inventors: Kirk W. Limbach, Dresher, PA (US); Christopher D. Frick, Pottstown, PA (US); Dmitry A. Krapchetov, Lansdale, PA (US); Wen-Sheng Lee, Midland, MI (US); Victor J. Sussman, Midland, MI (US); Jeffrey A. Herron, Midland, MI (US)

(73) Assignees: Rohm and Haas Company, Collegeville, PA (US); Dow Global Technologies LLC, Midland, MI (US)

( * ) Notice: Subject to any disclaimer, the term of this patent is extended or adjusted under 35 U.S.C. 154(b) by 290 days.

(21) Appl. No.: 17/252,884

(22) PCT Filed: Jun. 20, 2019

(86) PCT No.: PCT/US2019/038147
§ 371 (c)(1),
(2) Date: Dec. 16, 2020

(87) PCT Pub. No.: WO2020/005689
PCT Pub. Date: Jan. 2, 2020

(65) Prior Publication Data
US 2021/0121856 A1  Apr. 29, 2021

Related U.S. Application Data

(60) Provisional application No. 62/691,127, filed on Jun. 28, 2018.

(51) Int. Cl.
| | | |
|---|---|---|
| *B01J 23/52* | (2006.01) | |
| *B01J 21/04* | (2006.01) | |
| *B01J 21/08* | (2006.01) | |
| *B01J 35/00* | (2006.01) | |
| *C07C 67/39* | (2006.01) | |
| *B01J 6/00* | (2006.01) | |
| *B01J 37/03* | (2006.01) | |

(52) U.S. Cl.
CPC .............. *B01J 23/52* (2013.01); *B01J 21/04* (2013.01); *B01J 21/08* (2013.01); *B01J 35/008* (2013.01); *C07C 67/39* (2013.01); *B01J 6/001* (2013.01); *B01J 37/031* (2013.01)

(58) Field of Classification Search
CPC ... B01J 23/52; B01J 21/08; B01J 21/04; B01J 35/008; C07C 67/39
See application file for complete search history.

(56) References Cited

U.S. PATENT DOCUMENTS

| | | |
|---|---|---|
| 4,249,019 A | 2/1981 | Tamura et al. |
| 4,518,796 A | 5/1985 | Aoshima et al. |
| 4,520,125 A | 5/1985 | Baer et al. |
| 5,969,178 A | 10/1999 | Okamoto et al. |
| 6,040,472 A | 3/2000 | Yamamatsu et al. |
| 6,228,800 B1 | 5/2001 | Yamaguchi et al. |
| 7,326,806 B2 * | 2/2008 | Hayashi ................ B01J 35/002 560/208 |
| 8,461,373 B2 | 6/2013 | Suzuki et al. |
| 8,614,349 B2 | 12/2013 | Yokota et al. |
| 9,511,351 B2 | 12/2016 | Feaviour |
| 9,617,199 B2 | 4/2017 | Krill et al. |
| 11,207,664 B2 * | 12/2021 | Sussman ................ B01J 35/023 |
| 2016/0280628 A1 | 9/2016 | Krill et al. |
| 2018/0001307 A1 | 1/2018 | Lygin et al. |
| 2018/0326400 A1 | 11/2018 | Lygin et al. |
| 2019/0084914 A1 | 3/2019 | Krill et al. |

FOREIGN PATENT DOCUMENTS

| | | | |
|---|---|---|---|
| CN | 1931824 | 3/2007 | |
| CN | 107519892 | 12/2017 | |
| WO | 2009022544 | 2/2009 | |
| WO | 2016113106 | 7/2016 | |
| WO | 2017028905 | 2/2017 | |
| WO | WO-2017028905 A1 * | 2/2017 | ............. B01J 21/04 |
| WO | 2017084969 | 5/2017 | |
| WO | 2019022887 | 1/2019 | |
| WO | 2019057458 | 3/2019 | |
| WO | 2019060192 | 3/2019 | |
| WO | 2019139719 | 7/2019 | |
| WO | 2019139720 | 7/2019 | |

* cited by examiner

*Primary Examiner* — Yong L Chu
(74) *Attorney, Agent, or Firm* — Brian L. Mutschler

(57) ABSTRACT

A heterogeneous catalyst comprising a support and gold, wherein: (i) said support comprises alumina, (ii) said catalyst comprises from 0.1 to 5 wt % of gold, (iii) at least 90 wt % of the gold is in the outer 60% of catalyst volume, and (iv) particles of the catalyst have an average diameter from 200 microns to 30 mm; wherein weight percentages are based on weight of the catalyst.

13 Claims, No Drawings

HETEROGENEOUS CATALYST

BACKGROUND OF THE INVENTION

The invention relates to a heterogeneous catalyst. The catalyst is especially useful in a process for preparing methyl methacrylate from methacrolein and methanol.

Heterogeneous catalysts having noble metals supported on silica in combination with alumina and other elements are known, see e.g. U.S. Pat. No. 7,326,806B2. However, there is a need for additional catalyst particles with improved properties.

SUMMARY OF THE INVENTION

The present invention is directed to a heterogeneous catalyst comprising a support and gold, wherein: (i) said support comprises alumina, (ii) said catalyst comprises from 0.1 to 5 wt % of gold, (iii) at least 90 wt % of the gold is in the outer 60% of catalyst volume, and (iv) particles of the catalyst have an average diameter from 200 microns to 30 mm; wherein weight percentages are based on weight of the catalyst.

The present invention is further directed to a catalyst bed comprising particles of the heterogeneous catalyst.

The present invention is further directed to a method for preparing methyl methacrylate from methacrolein and methanol; said method comprising contacting a mixture comprising methacrolein, methanol and oxygen with a catalyst bed comprising particles of the heterogeneous catalyst.

DETAILED DESCRIPTION OF THE INVENTION

All percentage compositions are weight percentages (wt %), and all temperatures are in ° C., unless otherwise indicated. A "metal" is an element in groups 1 through 12 of the periodic table, excluding hydrogen, plus aluminum, gallium, indium, thallium, tin, lead and bismuth. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters.

Preferably the support has a surface area greater than 10 $m^2/g$, preferably greater than 30 $m^2/g$, preferably greater than 50 $m^2/g$, preferably greater than 100 $m^2/g$, preferably greater than 120 $m^2/g$. In portions of the catalyst which comprise little or no gold, the support may have a surface area of less than 50 $m^2/g$, preferably less than 20 $m^2/g$. Preferably, the catalyst particle comprises at least 0.1 wt % alumina, preferably at least 0.2 wt %, preferably at least 0.3 wt %; preferably no more than 95 wt %, preferably no more than 90 wt %, preferably no more than 80 wt %, preferably no more than 70 wt %, preferably no more than 60 wt %, preferably no more than 50 wt %, preferably no more than 40 wt %, preferably no more than 30 wt %, preferably no more than 20 wt %, preferably no more than 10 wt %, preferably no more than 5 wt %. Preferably, the catalyst particle is a silica particle comprising the aforementioned amounts of alumina. Preferably, the catalyst particle is an alumina particle.

Preferably, the aspect ratio of the catalyst particle is no more than 10:1, preferably no more than 5:1, preferably no more than 3:1, preferably no more than 2:1, preferably no more than 1.5:1, preferably no more than 1.1:1. Preferred shapes for the particle include spheres, cylinders, rectangular solids, rings, multi-lobed shapes (e.g., cloverleaf cross section), shapes having multiple holes and "wagon wheels," preferably spheres. Irregular shapes may also be used.

Preferably, at least 90 wt % of the gold is in the outer 60% of catalyst volume (i.e., the volume of an average catalyst particle), preferably in the outer 50%, preferably in the outer 40%, preferably the outer 30%, preferably the outer 25%. Preferably, the outer volume of any particle shape is calculated for a volume having a constant distance from its inner surface to its outer surface (the surface of the particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the gold is in the outer volume of the catalyst, preferably at least 97 wt %, preferably at least 99 wt %. Preferably, at least 90 wt % (preferably at least 95 wt %, preferably at least 97 wt %, preferably at least 99 wt %) of the gold is within a distance from the surface that is no more than 15% of the catalyst diameter, preferably no more than 13%, preferably no more than 10%, preferably no more than 8%. Distance from the surface is measured along a line which is perpendicular to the surface.

Preferably, the average diameter of the catalyst particle is at least 300 microns, preferably at least 400 microns, preferably at least 500 microns, preferably at least 600 microns, preferably at least 700 microns, preferably at least 800 microns; preferably no more than 20 mm, preferably no more than 10 mm, preferably no more than 5 mm. The average diameter of the support and the average diameter of the final catalyst particle are not significantly different.

Preferably, the amount of gold as a percentage of the catalyst (gold and the support) is from 0.2 to 5 wt %, preferably at least 0.3 wt %, preferably at least 0.5 wt %, preferably at least 0.7 wt %, preferably at least 0.9 wt %; preferably no more than 4 wt %, preferably no more than 3 wt %, preferably no more than 2.5 wt %.

Preferably, the support is produced by precipitating on a silica particle an aluminum salt. Preferably, the resulting material is then treated by calcination, reduction, or other treatments known to those skilled in the art to decompose the metal salts into metals or metal oxides. Preferably, the gold is precipitated from an aqueous solution of metal salts in the presence of the support. Preferably, the solution contains an acid such as nitric acid, sulfuric acid, hydrochloric acid, acetic acid or others. Preferably, the solution contains a sulfur-containing acid, e.g., thiomalic acid, preferably a carboxylic acid, e.g., citric or oxalic acid as well. Preferably, the sulfur-containing acid is present in a concentration of 1 to 10 wt % (preferably 3 to 8%). Preferably, the carboxylic acid is present in an amount from 0.1 to 25 wt % (preferably 0.5 to 15 wt %). Preferably, the weight ratio of sulfur to acid is 0.1:1 to 5:1, preferably from 0.2:1 to 3:1. Preferably, the support is washed with ammonium hydroxide prior to addition of gold precursor, preferably to remove chloride content to a level below 100 ppm in the bulk support, preferably below 50 ppm. Preferably, aluminum is precipitated from an aqueous solution of metal salts in the presence of the support. Preferred aluminum salts include aluminum nitrate, aluminum sulfate, aluminum chloride, aluminum hydroxide and aluminum oxide; preferably aluminum nitrate, aluminum sulfate or aluminum chloride. Preferred gold salts include tetrachloroauric acid, sodium aurothiosulfate, sodium aurothiomalate and gold hydroxide. In one preferred embodiment, the support is produced by an incipient wetness technique in which an aqueous solution of an aluminum precursor salt is added to a silica particle such that the pores are filled with the solution and the water is then removed by drying. Preferably, the resulting material is then treated by calcination, reduction, or other treatments known to those skilled in the art to decompose the metal salts into metals or metal oxides. Preferably, gold is added to an alumina or alumina-modified silica support by incipient wetness, followed by drying, and preferably by calcination.

Calcinations preferably are carried out at a temperature from 250° C. to 600° C.; preferably at least 300° C., preferably no more than 550° C. Preferably, the temperature is increased in a stepwise or continuous fashion to the ultimate calcination temperature.

In another preferred embodiment, the catalyst is produced by deposition precipitation in which a porous silica comprising alumina is immersed in an aqueous solution containing a suitable gold precursor salt and that salt is then made to interact with the surface of the inorganic oxide by adjusting the pH of the solution. The resulting treated solid is then recovered (e.g. by filtration) and then converted into a finished catalyst by calcination, reduction, or other treatments known to those skilled in the art to decompose the gold salts into metals or metal oxides.

The catalyst of this invention is useful in a process for producing methyl methacrylate (MMA) which comprises treating methacrolein with methanol in an oxidative esterification reactor (OER) containing a catalyst bed. The catalyst bed comprises the catalyst particles and is situated within the OER that fluid flow may occur through the catalyst bed. The catalyst particles in the catalyst bed typically are held in place by solid walls and by screens. In some configurations, the screens are on opposite ends of the catalyst bed and the solid walls are on the side(s), although in some configurations the catalyst bed may be enclosed entirely by screens. Preferred shapes for the catalyst bed include a cylinder, a rectangular solid and a cylindrical shell; preferably a cylinder. The OER further comprises a liquid phase comprising methacrolein, methanol and MMA and a gaseous phase comprising oxygen. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101.3 to 13890.8 kPa); preferably no more than 2000 kPa, preferably no more than 1500 kPa. Preferably, pH in the catalyst bed is from 4 to 10; preferably at least 4.5, preferably at least 5; preferably no greater than 9, preferably no greater than 8, preferably no greater than 7.5, preferably no greater than 7, preferably no greater than 6.5. Preferably, the catalyst bed is in a tubular continuous reactor.

The OER typically produces MMA, along with methacrylic acid and unreacted methanol. Preferably, methanol and methacrolein are fed to the reactor containing the fixed bed in a methanol:methacrolein molar ratio from 1:10 to 100:1, preferably from 1:2 to 20:1, preferably from 1:1 to 10:1. Preferably, the fixed bed further comprises inert materials. Preferred inert materials include, e.g., alumina, clay, glass, silica carbide and quartz. Preferably the inert materials are in the size range for the catalyst or smaller. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts.

EXAMPLES

Example #1

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel. Catalyst #1, as well as some other example were run in this manner Catalyst #1 Preparation:

Catalyst #1 was prepared by an incipient wetness technique using 5 g of Norpro 3.2 mm alumina spherical pellets as a starting support material and adding to that a solution consisting of 0.19 g of sodium gold thiosulfate, 0.2 g of mercaptosuccinic acid, 0.06 g of citric acid monohydrate and approximately 5 g DI water which had been stirred for 30 min prior to addition. The catalyst was then placed inside a box oven with constant air purging of approximately 50 LPH at room temperature for 1 hour and then the calcined at 400° C. using a ramping temperature of 5° C./min and holding at 400° C. for 4 hours.

Example #2

Batch Recycle Fixed Bed Bubble Column Reactor Operation:

A batch recycle reactor was used as described in Example #1

Catalyst #2 Preparation:

Catalyst #2 was prepared by an incipient wetness technique using 10 g of Norpro 3.2 mm alumina spherical pellets as a starting support material and adding to that a solution consisting of 0.39 g of sodium gold thiosulfate and 0.04 g of thiomalic acid in 10 g of DI water which had been stirred for 30 min prior to addition. The catalyst was then placed inside a box oven with constant air purging of approximately 50

LPH at 120° C. for 1 hour and then the calcined at 400° C. using a ramping temperature of 5° C./min and holding at 400° C. for 4 hours.

Example #3

Single Pass Fixed Bed Bubble Column Reactor Operation:

A feed consisting of 20 wt % methacrolein, 200 ppm inhibitor, and a balance of methanol was fed at a rate of 40 g/hr to a ⅜" stainless steel tubular reactor containing a short front section of borosilicate glass beads followed by 5 g of catalyst. Catalyst #2 was utilized. A gas containing 8% oxygen in nitrogen was also feed to the reactor at a rate sufficient to obtain 4.5% $O_2$ in the vent. The reactor was operated at 60° C. and 160 psig. The product of the reactor was sent to a liquid-vapor separator and the vapor was sent to a condenser with liquid return and non-condensable gases going to the vent. Results are described in the below table.

Catalyst #3 Preparation:

Catalyst #3 was prepared by an incipient wetness technique using 20 g of Fuji Silysia Chemical, Ltd. CARiACT Q-10 support as the starting material and adding aluminum to the support material. Specifically, 13.8 g of aluminum nitrate nonahydrate was dissolved in 20 g deionized water. Salt solution was added in very small droplets to the support in a rotating drum type equipment to ensure even distribution of the solution to the support material. The solution was at 80° C. when added. The modified support material was then dried under slight vacuum at 60° C. for 4 hrs and then calcined in air at ambient pressure by ramping the temperature at 5° C. per minute from ambient to 125° C., held for 1 hr and then ramped at 5° C. per minute up to 250° C. and held for 1 hr, then ramped at 5° C. per minute to 350° C. and held for 1 hr and finally ramped at 5° C. per minute to 450° C. and held for 4 hrs. Gold was then added to the support by incipient wetness technique utilizing 0.83 g of sodium aurothiosulfate in 10 g of deionized water at 40° C. The resulting catalyst was dried and calcined in air using the same heating profile as above. Analysis with a scanning electron microscope (SEM) equipped with energy-dispersive spectroscopy (EDS) of the catalyst clearly indicates that an eggshell deposition of both Al and Au exists with the Au preferentially located only where Al was deposited. The Al and Au eggshell thickness was found to be approximately 1 micron.

Example #4 Comparative

Batch Recycle Fixed Bed Bubble Column Reactor Operation:

A batch recycle reactor was used as described in Example #1

Catalyst #4 Preparation:

Catalyst #4 was prepared by incipient wetness of 4.1 g sodium gold thiosulfate dissolved in 100 g of water to make an aqueous solution and then placed on 100 g of Fuji Silysia Chemical, Ltd. CARiACT Q-20 silica support material. The sample was dried at 120° C. for 1 hr followed by calcination at 400° C. for 4 hr. Gold loading was approximately uniform in the catalyst.

| Catalyst # | Catalyst Description | Egg-shell Thickness[2] (microns) | Volume Percent Egg-Shell (%) | STY (mol/ kg-hr) | Normalized MMA Selectivity[1] (%) |
| --- | --- | --- | --- | --- | --- |
| 1 | Au/Al | 60 | 11 | 5.6 | 99.0 |
| 2 | Au/Al | 60 | 11 | 4.8 | 99.0 |
| 3 | Au/Al-SiO$_2$ | 1 | 0.6 | 6.1 | 97.9 |
| 4 comparative | Au/SiO$_2$ | Uniform (no eggshell) | na | 1.75 | 99.1 |

[1]The normalized MMA selectivity is the percent MMA among products originating as methacrolein reactant.
[2]Distance from particle surface in which at least 50 wt % of Au is present (SEM/EDS).
[3]Catalyst #3 is estimated from SEM/EDS to have 0.5 wt % alumina.
[4]STY is the space time yield in mol MMA per Kg catalyst hour.

The gold content of all catalysts was in the range from 1.1 to 1.5 wt %.

For Catalyst #2, ca. 95% of the gold was within the outer 200 microns, i.e., outer 33% of volume, while for Comp. Cat. 4, ca. 95% was within the outer 1000 microns (outer 95% of volume)

SEM/EDS of Eggshell Examples

Sample Imaging and EDS cross-section mapping: The SEM-EDS imaging was performed on a Hitachi SU-8230 equipped with Bruker AXS XFlash 6160 FlatQUAD energy dispersive X-ray spectrometer (EDS). Microscope working distance was 15 mm, the accelerating voltage was 15 keV, the beam current was 20 nA. The beam limiting aperture was set either to 1 or 0. Typical X-ray count rates were between 100 and 200 kcps. Maps were collected for 5 min. with a map size of 1000×750 pixels. Maps were generated using the Au M line at 2.1 keV, Al K at 1.5 keV, and S Kα at 2.4 keV.

The invention claimed is:

1. A heterogeneous catalyst comprising a support and gold, wherein: (i) said support comprises 0.1 to 15 wt % alumina and 60 to 95 wt % silica, (ii) said catalyst comprises from 0.9 to 4 wt % of gold, (iii) at least 90 wt % of the gold is in the outer 60% of catalyst volume, and (iv) particles of the catalyst have an average diameter from 300 microns to 30 mm; wherein weight percentages are based on weight of the catalyst.

2. The catalyst of claim 1 in which particles of the catalyst have an average diameter from 300 microns to 20 mm.

3. The catalyst of claim 2 in which at least 95 wt % of the gold is in the outer 50% of catalyst volume.

4. The catalyst of claim 3 in which the catalyst comprises 0.9 to 3 wt % of gold.

5. A catalyst bed which comprises (a) a heterogeneous catalyst comprising a support and gold, wherein: (i) said support comprises 0.1 to 15 wt % alumina and 60 to 95 wt % silica, (ii) said catalyst comprises from 0.9 to 4 wt % of gold, (iii) at least 90 wt % of the gold is in the outer 60% of catalyst volume, and (iv) particles of the catalyst have an average diameter from 300 microns to 30 mm; wherein weight percentages are based on weight of the catalyst, and (b) a liquid phase comprising methacrolein, methanol and methyl methacrylate.

6. The catalyst bed of claim 5 in which the catalyst has an average diameter from 500 microns to 10 mm and the catalyst bed further comprises a gaseous phase comprising oxygen.

7. The catalyst bed of claim 6 in which the catalyst comprises 0.9 to 3 wt % gold.

8. A method for preparing methyl methacrylate from methacrolein and methanol; said method comprising contacting a mixture comprising methacrolein, methanol and oxygen with a catalyst bed comprising a heterogeneous catalyst comprising a support and gold, wherein: (i) said support comprises 0.1 to 15 wt % alumina and 60 to 95 wt % silica, (ii) said catalyst comprises from 0.9 to 4 wt % of gold, (iii) at least 90 wt % of the gold is in the outer 60% of catalyst volume, and (iv) particles of the catalyst particle have an average diameter from microns to 30 mm; wherein weight percentages are based on weight of the catalyst.

9. The method of claim 8 in which the catalyst has an average diameter from 500 microns to 10 mm.

10. The method of claim 9 in which the catalyst comprises 0.9 to 3 wt % gold.

11. The catalyst of claim 1 in which the catalyst comprises 0.9 to 2.5 wt % of gold.

12. The catalyst bed of claim 5 in which the catalyst comprises 0.9 to 2.5 wt % of gold.

13. The method of claim 8 in which the catalyst comprises 0.9 to 2.5 wt % of gold.

* * * * *